(12) United States Patent
Wei et al.

(10) Patent No.: US 7,641,922 B2
(45) Date of Patent: Jan. 5, 2010

(54) PREPARATION AND APPLICATION OF TRANSHINTOTALPHENOLIC ACID

(75) Inventors: Feng Wei, Tianjin (CN); Hongshui Yue, Taijin (CN); Dekun Li, Taijin (CN); Jiangxiao Sun, Taijin (CN); Zhengliang Ye, Tianjin (CN); Xu Li, Taijin (CN)

(73) Assignee: Tianjin Tasly Pharmaceutical Co., Ltd., Beichen District, Taijin ( * ) Notice: Subject to any disclaimer, the term of this patent is extended or adjusted under 35 U.S.C. 154(b) by 588 days.

(21) Appl. No.: 10/515,963

(22) PCT Filed: May 21, 2003

(86) PCT No.: PCT/CN03/00375

§ 371 (c)(1),
(2), (4) Date: Nov. 23, 2004

(87) PCT Pub. No.: WO03/099759

PCT Pub. Date: Dec. 4, 2003

(65) Prior Publication Data

US 2005/0159491 A1  Jul. 21, 2005

(30) Foreign Application Priority Data

May 23, 2002  (CN) ............................... 02 1 17923

(51) Int. Cl.
*A61K 36/00* (2006.01)
*A61K 36/537* (2006.01)
(52) U.S. Cl. ...................... 424/746; 424/725
(58) Field of Classification Search .............. 424/746, 424/725
See application file for complete search history.

(56) References Cited

U.S. PATENT DOCUMENTS 6,043,276 A * 3/2000 Han et al. .................... 514/532
6,299,910 B1 * 10/2001 Xu et al. ..................... 424/746

FOREIGN PATENT DOCUMENTS

| CN | 1 247 855 | 3/2000 |
| CN | 1247855 A | 3/2000 |
| CN | 1270809 A | 10/2000 |
| CN | 1 342 638 | 4/2002 |
| CN | 1342638 A | 4/2002 |
| CN | 1384090 A | 12/2002 |
| WO | WO 98/24460 | 6/1998 |

OTHER PUBLICATIONS

Takashi Tanaka, et al. "Magnesium and Ammonium-Potassium Lithospermates B" 1989, 37(2) Chemical Pharmaceutical Bulletin, 340-344.
Takako Yokozawa, et al. "Isolation of the Active Component Having the Uremia-Preventive Effect from Salviae Miltiorrhizae Radix Extract" 1988, 36(1), Chemical Pharmaceutical Bulletin, 316-320.
Chan et al., "*The effects of Danshen (Salvia miltiorrhiza) on warfarin pharmacodynamics and pharmacokinetics of warfarin enantiomers in rats*," Journal of Pharmacy and Pharmacology, 1995, 47(5), pp. 402-406.
Chan, "*Drug interactions as a cause of overanticoagulation and bleedings in Chinese patients receiving warfaren*," International Journal of Clinical Pharmacology and Therapeutics, 1998, 36(7), pp. 403-405.
Chan, "*Interaction between warfarin and danshen (Salvia miltiorrhiza)*,"The Annals of Pharmacotherapy, 2001, 35(4), pp. 501-504.
Dasgupta A. et al. "*In vivo digoxin-like immunoreactivity in mice and interference of Chinese medicine Danshen in serum digoxin measurement: elimination of interference by using a chemiluminescent assay*," Clinica Chimica Acta, 2002, 317(1), pp. 231-234.
Du et al., "*Protective effects of salvianolic acid A against impairment of memory induced by cerebral ischemia-reperfusion in mice*," Chin Med J., 1997, 110(1), pp. 65-68.
Du et al., "*Salvianolic acid B protects the memory functions against transient cerebral ischemia in mice*," J. Asian. Nat. Prod. Res., 2000, 2(2), pp. 145-152.
Fugh-Berman, "*Herbs and dietary supplements in the prevention and treatment of cardiovascular disease*," Preventive Cardiology, 2000, 3(1), pp. 24-32.
Heck et al., "*Potential interactions between alternative therapies and warfarin*," American Journal of Health-System Pharmacy, 2000, 57(13), pp. 1221-1227.
Huang et al., "*Hemodynamic effects of Salvia miltiorrhiza on cirrhotic rats*," Canadian Journal of Physiology and Pharmacology, 2001, 79(7), pp. 566-572.

(Continued)

Primary Examiner—Taylor Victor Oh
(74) Attorney, Agent, or Firm—Fish & Richardson P.C.

(57) ABSTRACT

A process for preparing tanshintotalphenolic acid and the use of the product are disclosed. The process comprises: tanshin is hot-extracted with water, the extract is separated and refined by polyamide column and macroporous adsorption resin column, and lyophilized to obtain tanshintotalphenolic acid. The yield of the final end product is more than 4 percent based on the amount of crude drug and the content of total-phenolic acid is more than 80 percent. The tanshintotalphenolic acid obtained can be used as the medicine for preventing and treating cerebrovascular and cardiovascular diseases and so on.

14 Claims, No Drawings

OTHER PUBLICATIONS

Ji et al., "*Salvia miltiorrhiza and ischemic diseases*," Acta Pharmacol Sin. 2000, 21(12), pp. 1089-1094.

Kang et al., "*Anti-hypertensive effect of water extract of danshen on renovascular hypertension through inhibition of the renin angiotensin system*," American Journal of Chinese Medicine, 2002, 30(1), pp. 87-93.

Li, "*Protective effects of schisanhenol, salvianolic acid A and SY-L on oxidative stress induced injuries of cerebral cells and their mechanisms*," Sheng Li Ke Xue Jin Zhan, 1998, 29(1), pp. 35-38.

Liu et al, "*Effect of Salvia miltiorrhiza on coronary collateral circulation in dogs with experimental acute myocardial infarction*," Journal of the Tongji Medical University, 1999, 19(1), pp. 40-41 and 69.

Lo et al., "*The effects of danshen (Salvia miltiorrhiza) on pharmacokinetics and pharmacodynamics of warfarin in rats*," European Journal of Drug Metabolism and Pharmacokinetics, 1992, 17(4), pp. 257-262.

Oh et al., "*Salvia miltiorrhiza inhibits biliary obstruction-induced hepatocyte apoptosis by cytoplasmic sequestration of p53*," Toxicology and Applied Pharmacology, 2002, 182(1), pp. 27-33.

Peng et al., "*Effects of danshen and shengmaiye on glomerulosclerosis by adriamycin in rats*," Hunan Yi Ke Da Xue Xue Bao. 1999, 24(4), pp. 332-334.

Sun et al., "*Study on activating blood and eliminating stasis of guanxin dansheng capsule*," Zhong Yao Cai., Feb. 2002, 25(2), pp. 120-121.

Yokozawa et al., "*Isolation of the active component having the uremia-preventive effect from Salviae mlitiorrhizae radix extract*," Chem. Pharm. Bull., 1988, vol. 36, No. 1, 316-320.

Tanaka et al., "*Magnesium and ammonium-potassium lithospermates B, the active principles having a uremia-preventive effect from Salvia miltiorrhiza*" Chem. Pharm. Bull, 1989, vol. 37, No. 2, pp. 340-344.

Tam et al., "*Warfarin interactions with Chinese traditional medicines: danshen and methyl salicylate medicated oil*," Australia and New Zealand Journal of Medicine, 1995, 25, pp. 258.

Tan et al., "*Influence of Salvia miltiorrhizae and astragalus membranaceus on hemodynamics and liver fibrosis indexes in liver cirrhotic patients with portal hypertension*," Zhongguo Zhong Xi Yi Jie He Za Zhi, 2001, 21(5), pp. 351-353.

Wahed, "*Positive and negative in vitro interference of Chinese medicine dan shen in serum digoxin measurement. Elimination of interference by monitoring free digoxin concentration*," American Journal of Clinical Pathology, 2001, 116(3), pp. 403-408.

Wang et al., "*A new platelet aggregation inhibitor from Salvia miltiorrhiza*," Planta Medica, 1989, 55, pp. 390-391.

Wu et al., "*Cytotoxic activities of tanshinones against human carcinoma cell lines*," American Journal of Chinese Medicine, 1991, 19(3-4), pp. 207-216.

Xiuqiao et al., "*Pharmacodynamic Comparison between Sanhuang Decoction for Purging Stomach-fire and Its Concentrated Granule*" 2002, 25(2), pp. 119-120.

Youming et al. "*Effects of danshen and shengmaiye on glomerulosclerosis by adriamycin in rats*" Bull. of Hunan Med. Univ. 1999, 24(4), pp. 332-334.

Zou et al., "*Antithrombotic and antiplatelet effects of rosmarinic acid, a water-soluble component isolated from radix Salviae miltiorrhizae (danshen)*," Acta Pharmaceutica Sinica, 1993, 28(4), pp. 241-245.

\* cited by examiner

PREPARATION AND APPLICATION OF TRANSHINTOTALPHENOLIC ACID

FIELD OF THE INVENTION

The present invention relates to an extract of Traditional Chinese Medicine (TCM). More particularly, the present invention relates to a refined total phenolic acid extracted from TCM Danshen and the method for extracting the same.

BACKGROUND OF THE INVENTION

Danshen, also known by its botanical name Radix Salvia Miltiorrhizae, is one of the most common-used traditional Chinese medicines (TCM) in China. It mainly consists of two categories of chemical ingredients, namely the water-soluble and the non water-soluble. Dating back to the early 20th century, the chief research on these ingredients has always been concentrated on the non water-soluble ones represented by tashinone, and achieved great success after decades of efforts. It is not until the beginning of 1980s that, after a lot of work, our scientists have studied Danshen's water-soluble ingredients, and first reported structure of the water-soluble one, Danshensu. Afterward, tens of water-soluble ones have also been discovered one after another with the definitive chemical structure. Subsequently it has been proven that, of the active ingredients in Danshen's water-soluble ones, the most effective is phenolic acid compounds, such as salvianoic acid A(1), B(2), C(3), D(4), E(5), F(8), G(9), H(11), I(12), J(13), rosmarinci acid (6), alkannic acid (7), isosalvianoic acid C(10), glucoside of rosmarinci acid(14), etc. (Lian-Niang Li, J. Chinese Pharmaceutical Sciences 1997, 6, 57-64). Pharmacologically, a variety of activities of these salvianolic acid compounds have already been reported. For example, Salvianolic acid A has significant protecting effects on cardiac muscle cell caused by ischemic reperfusion (I/R), and totalphenolic acid has strong anti-arrhythmia effect induced by I/R; Salvianolic acid A, B and totalphenolic acid have showed markedly protective effects against brain damage caused by I/R in rats by lowering content of MDA in brain tissues; there are plenty more other effects for the salvianolic acid as follows: anti-thrombus effects, protective effect on liver and kidney, anti-oxidation and inhibiting lipid super oxidation, as well scavenging puperoxide anion and free radical etc. (Du Guanhua etal, Basic medical science and clinics, 2000, 20 (5):10–14).

At present, a great number of processes of extracting Salviamolic acid have been reported, but most of them are mainly focused on passing resin column following extracting by water. For example, Takashi Tanaka et al revealed the method of extracting salvainolate (Chemical Pharmaceutical Bulletin, 1989, 37(2), 340–344). Besides, there have also been many other scientists who have adopted similar methods for extracting phenolic compounds from Danshen, such as Koji Hase et al (Planta Medica, 1997, 63, 22–26), Xu Yaming et al (China patent CN1247855A, published in March, 2000), Liu Ping et al (China patent CN1270809A, published in October, 2000), and Li Lianniang (China Patent Application No. 0114228.2, filed on September 2001). But all of above-mentioned processes for extracting have a common problem in industrialization, namely a great deal of water need to be concentrated. Because of the instability, the concentrating temperature of total salvainolic acid water decoction must be varying between 50° C. and 60° C., which accordingly will result in both the difficulties in techniques and rise in cost. Meanwhile, the lasting heating process, although between 50° C. and 60° C., will also produce a series of serious problems including instability, and therefore affect its quality and curative effect. Finally, all these problems make it almost impossible for the industrialization. Another shortcoming of these already-existing processes is that the low yield, generally between 2% and 3%, limits its application in the industry.

SUMMARY OF THE INVENTION

Accordingly, one object of the present invention is, obviating the drawbacks of the prior art, to provide a method for preparation of totalphenolic acid with high yield, low cost, good quality, and convenience of being applied in the industry.

DETAILED DESCRIPTION OF THE PREFERRED EMBODIMENTS

The present invention of preparing totalphenolic acid mainly consists of the following steps, namely decocting Danshen with hot water; separating the decoction with Polyamide column and macroporous adsorption resin.

The totalphenolic acid may be obtained by the following scheme:
(a) After the impurities is eliminated, the Danshen is cut into little sections or pulverized into crude powder, and decocted with hot water. The decoction is filtered after its pH value being adjusted to acidity.
(b) Applying said decoction on a polyamide column, and washing the column with water to neutral condition. Eluting the column with weak basic aqueous solution, and collecting the eluent.
(c) Applying the eluent on the macroporous adsorption resin column, after acidifying the basic eluent of step (b). At first, washing the column with water to neutral condition, and then eluting the column with hydrous or anhydrous lower alcohol. Afterward, collecting the eluent.
(d) Concentrating the eluent under reduced pressure until there is no ethanol, and drying it to obtain the total salvianolic acid.

In step (a), Danshen is extracted with hot water for 2 to 4 times, 0.5 to 2 h each, and the extracting temperature is 60 to 100° C., preferably 90 to 100° C.; the extract solution after each extracting process, alone or combined, preferably combined, is further treated; the pH value is adjusted with acid to less than 4, preferably below 2.

In step (b), the concentration of weak basic aqueous solution preferably is from 0.01% to 2%, most preferably 0.08% to 0.5%, and the common polyamide materials is used, for example, polycaprolactam (nylon-6).

In step (c), the common macroporous adsorbent resin is used, for example styrene-type adsorbent resin; the pH value of weak basic fractions are adjusted by acid to below 4, preferably below 2; the number of carbon atoms in lower ethanol ranges from 1 to 5, for example, the methanol, ethanol, etc.; the eluting concentration is 40% to 95%, preferably 60% to 95%. However, in view of the safety in large-scale industrialized production, lowering cost and process simplification, eluting by 95% ethanol is the best option to achieve satisfying purpose.

In step (d), if necessary, said concentrate is dried, such as by lyophilization, following being filtered with microporous filter membrane.

The totalphenolic acid produced by the method of this invention can be formulated into any kind of pharmaceutically acceptable dosage form, and can also be combined with other medicaments or active ingredients.

According to this invention, a totalphenolic acid of Danshen, produced by the method of this invention.

A pharmaceutical composition, including the totalphenolic acid of Danshen of this invention and pharmaceutically acceptable carrier or excipient.

Compared with the prior art, this invention has the following advantages:

1. Easiness of industrialization. In the prior art, a great deal of water need to be concentrated during the process, resulting in the difficulties in industrialization. Such a defect is overcome in the present invention, wherein, without heating and decompression, lot of water are surprisingly removed. Consequently, the processes and conditions are optimized with no energy consuming and environment pollution. So, with the advantages in respect of techniques or environmental protection, it is easy to bring about industrialization.
2. Reduction of loss in active ingredients. The present invention can effectively avoid a loss of active ingredients caused by precipitation with alcohol in prior art, and also prevent instability of totalphenolic acid in concentrating a lot of water. All these above would in effect avoid the losses and decomposition of the active ingredients during the process, so as to assure the stability of final product.
3. High yield. The yield of the products produced in the prior art (i.e. the dried totalphenolic acid powder) is only 2% –3% by weight based on the crude herbal medicine; while using the method of present invention, the yield is more than 4%, apparently better than that of the prior art. Moreover, the content of totalphenolic acid in the high quality final product is more than 80% with less impurity.
4. Lower cost. In the method of present invention, a great deal of water can be concentrated and removed without heating and decompression, effectively reducing the energy consumption and cost. In addition, the yield of the total phonelic acid by this invention is higher, and moreover its content in the final product is close to or higher than that of the prior art, that is to say, more products with equal or better quality will be produced from the same amount of crude herbal medicine. The lower cost will benefit a lot, not only in the industrialization, but also the patients' economic interests, accordingly bringing about a great social benefit.
5. The studies on animals also show the good effects of the totalphenolic acid produced by the method of present invention.

Protective Effect of the Totalphenolic Acid Against Cerebral Artery Ischemia in Rats 1. Materials and Methods
1) Animals: Male Wister rats, weighing from 200 to 220 g (Certificate No. SCXK(Beijing) 2002-003), are obtained from the Animal Center of Beijing Medical University.
2) Reagents: Chloral Hydrate purchased from Shenyang reagent factory, Liaoning, China, the batch number being 920401.
   Red tetrazoline (TTC) from Beijing chemical plant, the batch number being 810911.
3) Apparatus: High-frequency electric knife purchased from Beijing medical electronic apparatus factory.
   The SXP-1B operating microscope from Shanghai medical optical instrument factory.
4) Tested agents: The total phonetic acid produced by Tianjin Tasly Modern TCM institute according to the method of the present invention; and
   The total salvianolic acid produced by Institute of Materia Medica, Chinese Academy of Medical Sciences in accordance with the method of China Patent Application No. 01142288.2 filed on September, 2001.
   Xiangdan injection, as control drug, purchased from Ya an Sanjiu pharmaceutical Co. ltd, the bath number being 010901.
5) Formulation method of the tested agents and route of administration: The totalphenolic acid and Xiangdan injection are diluted into desired concentration with sterilized physiological saline, 10 mg/kg and 20 mg/kg for the totalphenolic acid, and 1 ml/kg (equal to 1 g/kg) for Xiangdan injection. By sublingual vein, both of these kinds of drugs are administered 30 minutes after ischemia.
6) Groups: All rats are randomly divided into the following groups: sham operation control group, ischemic control group, total phonetic acid (Institute of Materia Medica) 10 mg/kg and 20 mg/kg groups, total phonelic acid (Tasly) 10 mg/kg and 20 mg/kg groups.

2. Method
1) cerebral artery blockade (electric coagulation) ischemia in rats: Rats are anesthetized by intraperitoneal injection of Trichloracetic aldehyde, 350 mg/kg body weight, and fixed on a board in a left lateral position. Under the operating microscope, the skin is incised open via midline between the external auditory meatus and the canthus. The zygomatic orthopedics is exposed, and removed thoroughly with orthopedics rongeur. The fascia is nipped off along skull, and tempora fossa is exposed. Between the squamous orthopedics and mandible is gently propped up with retractor, and at the bottom of the skull the skull window is opened so as to uncover cerebral middle artery. The middle artery is burnt out with the high-frequency electric knife in order to block the blood flow, forming a model of cerebral local ischemia. After 30 minutes, the rats are administrated through sublingual vein, and sent back to cage for feed. The room temperature is rigorously kept between 24° C. and 25° C.
2) The measurement of cerebral infarct volume: 24 hours after the cerebral middle artery is blocked, the rats are beheaded and their cerebrums are taken out. The whole cerebrum is kept at 4° C. in a beaker filled with normal-saline in a refrigerator for 10 minutes, and then the olfactory bulb, the cerebellum and the low-set brain stem are removed. Along the coronal plane, the cerebrum is chipped into 5 slices, and put into 5 ml dyeing solutions containing 1.5 ml of 4% TTC and 0.1 ml of 1 mol/L di-potassium hydrogen phosphate, light-proof incubated in water bath 37° C. for 30 minutes. The slices of cerebrum are taken out and put into 10% formalin for solidification. As a result, the normal cerebral tissue is rose pink, and the ischemic one is white. The weight planimetry is used to measure the area of infarct, and further the percentage of the area of infarct to the whole cerebrum hemisphere is calculated.
3) The measurement of content of water in the cerebrum: 24 hours after blockade of the cerebral middle artery, the rats are executed, and the whole cerebrum is gently taken out. After that the olfactory bulb, the cerebellum and the low-set brain stem are taken away, the cerebrum is weighed (regarded as the cerebral wet weight). After that, the cerebrum is dried in an oven at 105° C. till that the weight is constant (about 48 hours), and is weighed again (referred to as the cerebral dry weight). The final content of water in the cerebrum is calculated with the following formula:

the content of water in the cerebrum=(the cerebral wet weight–the cerebral dry weight)/the cerebral wet weight×100%.

3. Result

Protective effect of the totalphenolic acid against the cerebral middle artery coagulation ischemia in rats

| group | dosage mg/kg | number of animal N | Volume of infarct (%) | the content of water (%) |
|---|---|---|---|---|
| sham operation control group | | 12 | 0 | 79.4586 ± 0.3402** |
| ischemic control group | | 10 | 7.0194 ± 4.389 | 80.4487 ± 0.8614 |
| Xiangdan injection | 1 ml/kg | 12 | 0.7553 ± 2.2188** | 79.4364 ± 0.5061** |
| total phonelic acid (Institute of Materia Medica) | 10 | 12 | 3.2919 ± 3.205# | 79.4723 ± 0.5475** |
| total phonelic acid (Institute of Materia Medica) | 20 | 12 | 1.5156 ± 2.7602* | 79.4806 ± 0.6819* |
| total phonelic acid (Tasly) | 10 | 10 | 2.8170 ± 3.2621# | 79.4529 ± 0.7693* |
| total phonelic acid (Tasly) | 20 | 10 | 1.5328 ± 3.2575* | 79.5914 ± 0.5843* | note:
(1) **$P < 0.01$, *$P < 0.05$, two-sided test, comparing with ischemic control group. #$P < 0.05$, one-sided test, compared with ischemic control group.
(2) 1 ml/kg the Xiang dan injection as a control is equal to 1 g/kg of crude herbal medicine;
10 mg/kg totalphenolic acid (Tasly) is equal to 0.25 g/kg of crude herbal medicine (calculated with yield being 4%); and 20 mg/kg totalphenolic acid (Tasly) is equal to 0.5 g/kg of crude herbal medicine (calculated with yield being 4%).

4. Conclusion

By using the method of coagulation in middle cerebral artery to attain cerebral ischemia in rats, the protective effect of the totalphenolic acid produced respectively by Tasly and Institute of Materia Medica on cerebral artery ischemic has been observed. The result revealed that, 30 min after administration in vein, 10 mg/kg and 20 mg/kg of both two kinds of phenolic acids could markedly alleviate cerebral edema and cerebral infarction caused by ischemia. Moreover, the said two kinds of phenolic acids had the same effect administered in the same dosage. All above studies have showed that two phenolic acids had the same effect of anti-cerebral ischemia.

The totalphenolic acid of this invention can be formulated into pharmaceutically acceptable dosage forms, including tablet, capsule, granules, oral liquid, sustained-release formulation, control-release formulation, gel, ointment, salve, cream, suppository, injection, powder, patch, dripping pill and suspension.

The totalphenolic acid of this invention can be used for the treatment of diseases, including cardiovascular and cerebrovascular disease, nephrosis, hepatopathy, pneumonia, pneumocardial disease, pancreatitis, diabetes mellitus, cervical syndrome, ocular fundus vascular disease, ocular fundus neuro-disease, migrain, chronic gastritis, dizziness, orthopedics disease, mountain sickness and senile dementia.

EMBODIMENTS

The following examples are offered for purposes of illustration only and are not intended to limit the scope of the invention in any way.

COMPARATIVE EXAMPLE

Totalphenolic acid is prepared according to the Chinese Patent Application No. 01142288.2, filed on September 2001.

5 Kg of Danshen herb is ground into crude powder, and is extracted at 100° C. for three times with deionized water added, specifically, extracted for 1 hour with 30 L water added the first time, and extracted for 0.5 hour with 15 L water added the second and third times respectively. The extract is concentrated to 5 L at 50° C. under reduced pressure and cooled. Into the concentrate 14 L of 95% ethanol is added. The mixture is allowed to stand over night and filtered. Under reduced pressure, the ethanol is recovered at 50° C. The obtained concentrate is applied on RA macroporous adsorption resin (mainly containing styrene and chrysophenine, and the weight of dried resin is 2 kg). The resin is washed with deionized water until that the eluent had no apparent α-naphthol reaction, and then eluted with 50% ethanol until that the eluent had no obvious phenolic hydroxyl reaction with iron sesquichloride potassium ferricyanide added. The fractions are concentrated at 50° C. under reduced pressure. The mixture is allowed to stand over night in a refrigerator, and filtered to produce the extract of Total salvianolic acid. The pH of the said extract is adjusted with 2% sodium hydroxid to 6.5, and the extract is freeze dried to produce 114 g of totalphenolic acid. The yield of the final product in crude drug is 2.3%. The analysis showed that the content of totalphenolic acid in final product amounted to 83.72%, and Salvianolic acid B was in amount of 54.41%.

Total salvianolic acid and Salvianolic acid B are analyzed according to the method of Chinese Patent Application No. 01142288.3 filed on September 2001.
(1) Salvianolic acid B: analyzed by HPLC at 288 nm. The Salvianolic acid B CRS is manufactured by Modern TCM Institute under Tianjin Tasly Group with purity of 98.0%.
(2) Total salvianolic acid: Content=F(A−B)+B wherein, A is the content of Total salvianolic acid calculated with the Salvianolic acid B as CRS by ultraviolet spectrophotometry;
B is the content of Salvianolic acid B by HPLC;
F is correction factor 0.626.

EXAMPLE 1

5 kg of Danshen herb is ground into crude powder, and is extracted at 100° C. at the state of lightly boiling for three times with deionized water, specifically, extracted for 1 hour with water (×5.5 fold) added the first time, and extracted for 0.5 hour with water (×3 fold) added the second and third times respectively. The extract is combined, and the pH thereof is adjusted with 10% hydrochloric acid to 2.0. The extract is filtered, and the filtrate is loaded on polyamide column (the amount of the dry resin is two-thirds of that of the crude herb). The column is washed with deionized water (×5 fold), and the washing is discarded. Then the column is eluted with 5 column volumes of the 0.1% aqueous solution of sodium bicarbonate. The fraction was collected, adjusted with 10% hydrochloric acid to pH 2.0, and is loaded on $D_{101}$ macro-porous resin column. The column is washed with deionized water to neutral condition and the washing is discarded. Then the column is eluted with 95% ethanol, and the colored belt is collected when it is eluted down. The fractions are concentrated under reduced pressure to entire dryness. The above concentrate is dissolved with water. The mixture is allowed to stand over night in refrigerator, and filtered by 0.3 μm mixed cellulose microporous membrane to produce extraction solution of Total salvianolic acid. Immediately after this totalphenolic acid is adjusted with 2% sodium hydroxide to pH 6.0, it is freeze dried to produce 221 g of freeze-dried powders of Total salvianolic acid. The yield of the final product is 4.4% based on the amount of the crude herb. The analysis according to the method of Chinese Patent Application No. 01142288.2 filed on September 2001 shows that, the totalphenolic acid amounts to 83.94%, and Salvianolic acid B is 53.73% in the final product.

EXAMPLE 2

5 kg of Danshen herb is ground into crude powder, and is extracted at 80° C. for three times with deionized water, specifically, extracted for 2 hours with water (×5.5 fold) added the first time, and extracted for 1 hour with water (×3 fold) added the second and third times respectively. The extracts are combined, and the pH thereof is adjusted with 5% sulfuric acid to 1. The extract is filtered, and the filtrate is loaded on polyamide column (the amount of the dry resin is two-thirds of that of the crude herb). The column is washed with deionized water (×5 fold), and the washing is discarded. Then the column is eluted with 4 column volumes of the 0.2% aqueous solution of sodium bicarbonate. The fractions are collected, adjusted with 5% sulfuric acid to a pH of 1, and is loaded on AB-8 macro-porous adsorption resin column. The column is washed with deionized water to neutral condition and the washing is discarded. Then the column is eluted with 60% ethanol, and the colored belt is collected when it is eluted down. The fractions are concentrated under the reduced pressure until it had no smell of ethanol. The mixture is allowed to stand over night in refrigerator, and filtered by 0.3 μm mixed cellulose micro-porous membrane to produce extraction solution of Total salvianolic acid. Immediately after this totalphenolic acid is adjusted with 2% sodium hydroxide to pH 6.0, it is freeze dried to produce 227 g of freeze-dried powders of Total salvianolic acid. The yield of the final product is 4.5% based on the amount of the crude herb. The analysis according to the method of Chinese Patent Application No. 01142288.2 filed on September 2001 shows that, the totalphenolic acid amounts to 83.15%, and Salvianolic acid B is 54.03% in the final product.

EXAMPLE 3

5 kg of Danshen herb is ground into crude powder, and is extracted at 100° C. at the state of lightly boiling for three times with deionized water, specifically, extracted for 1 hour with water (×5.5 fold) added the first time, and extracted for 0.5 hour with water (×3 fold) added the second and third times respectively. The extract is combined, and the pH thereof is adjusted with 10% hydrochloric acid to 2.0. The extract is filtered, and the filtrate is loaded on polyamide column (the amount of the dry resin is two-thirds of that of the crude herb). The column is washed with deionized water (×5 fold), and the washing is discarded. Then the column is eluted with 5 column volumes of the 0.1% aqueous solution of sodium bicarbonate. The fractions are collected, adjusted with 10% hydrochloric acid to a pH of 2.0, and is loaded on RA macro-porous resin column. The column is washed with deionized water to neutral condition and the washing is discarded. Then the column is eluted with 60% Methanol, and the colored belt is collected when it is eluted down. The fractions are concentrated under the reduced pressure until it had no smell of ethanol. The mixture is allowed to stand over night in refrigerator, and filter by 0.3 μm mixed cellulose micro-porous membrane to produce extraction solution of Total salvianolic acid. Immediately after this totalphenolic acid is adjusted with 2% sodium hydroxide to pH 6.0, it is freeze dried to produce 224 g of freeze-dried powders of Total salvianolic acid. The yield of the final product is 4.5% based on the amount of the crude herb. The analysis according to the method of Chinese Patent Application No. 01142288.2 filed on September 2001 shows that, the totalphenolic acid amounts to 84.02%, and Salvianolic acid B is 54.17% in the final product.

EXAMPLE 4

Formula of Total Salvianolic Acid Capsule

| | |
|---|---|
| Total salvianolic acid | 240 g |
| Microcrystalline cellulose | 40 g |
| Talcum powder | 1.4% |
| 3% ethanol solution of polyvidone | appropriate |
| 1000 capsules are produced. | |

Total salvianolic acid and microcrystalline cellulose are mixed thoroughly. 3% ethanol solution of polyvidone is added into the mixture to make soft stuff. It is sifted through 18-mesh screen sieve to give granules, and dried at 60° C. for 30 to 45 min. Then, talcum powder is added, and the mixture is stirred and filled into No. 1 capsule shell to produce capsules each of which contains 240 mg.

EXAMPLE 5

Formula of of Total Salvianolic Acid Tablet

| | |
|---|---|
| Total salvianolic acid | 240 g |
| Microcrystalline cellulose | 40 g |
| Talcum powder | 1.4% |
| 3% ethanol solution of polyvidone | appropriate |
| 1000 tablets are produced. | |

Total salvianolic acid and microcrystalline cellulose are mixed thoroughly. 3% ethanol solution of polyvidone is added into the mixture to make soft stuff. It is sifted through 18-mesh screen sieve to give granules, and dried at 60° C. for 30 to 45 min. Then, talcum powders are added, and the mixture is stirred and tableted.

EXAMPLE 6

Formula of Total Salvianolic Acid Granula

| | |
|---|---|
| Total salvianolic acid | 240 g |
| Microcrystalline cellulose | 40 g |
| Talcum powder | 1.4% |

|   |   |
|---|---|
| 3% ethanol solution of polyvidone | appropriate |

500 sachets are produced.

Total salvianolic acid and microcrystalline cellulose are mixed thoroughly. 3% ethanol solution of polyvidone is added into the mixture to make soft stuff. It is sifted through 18-mesh screen sieve to give granules, and dried at 60° C. for 30 to 45 min, and filled into sachets.

EXAMPLE 7

Formula of Total Salvianolic Acid Powder for Injection

|   |   |
|---|---|
| Total salvianolic acid | 100 g |
| Mannite | 30 g |
| Antallin | 5 g |
| Distilled water | 5 ml |

The above ingredients are mixed well, lyophilized, and filled into 1000 vials.

The invention claimed is:

1. A method for the preparation of total salvianolic acid comprising the steps of:
   (a) extracting Danshen with water to produce a Danshen extract, acidifying the extract and filtering the extract;
   (b) applying the Danshen extract to a polyamide column, washing the polyamide column with water until neutral, discarding the washings, and collecting fractions eluted from the polyamide column with a weak basic aqueous solution;
   (c) acidifying the fractions eluted from the polyamide column, applying the fractions to a macroporous adsorption resin column, washing the column with water to achieve neutrality, discarding the washings, and collecting eluate from the macroporous adsorption resin column with a hydrous or anhydrous lower alcohol, wherein the eluate is further optionally concentrated and dried.

2. The method of claim 1, wherein the step of extracting Danshen with water is repeated 2-4 times for 0.5-2 hours each time.

3. The method of claim 1, wherein the step of extracting Danshen with water is carried out at 60-100° C.

4. The method of claim 1, wherein the step of extracting Danshen with water is carried out at 90-100° C.

5. The method of claim 1, wherein the pH of the Danshen extract is adjusted to below 4, and the pH of the fractions eluted from the polyamide column adjusted to below 4.

6. The method of claim 1, wherein the pH of the Danshen extract is adjusted to below 2, and the pH of the fractions eluted from the polyamide column is adjusted with hydrochloric acid or sulfuric acid to a value below 2.

7. The method of claim 1, wherein the fractions eluted from the polyamide column are eluted with 0.01-2% of aqueous weak basic solution.

8. The method of claim 1, wherein the fractions eluted from the polyamide column are eluted with 0.08-0.5% of an aqueous solution of sodium hydrogen carbonate.

9. The method of claim 1, wherein the macroporous adsorption resin is a type of styrene.

10. The method of claim 1, wherein the hydrous or anhydrous lower alcohol is a lower $C_1$-$C_5$ alcohol.

11. The method of claim 1, wherein the hydrous lower alcohol is an aqueous ethanol with a concentration of 40-95%.

12. The method of claim 10, wherein the concentration of the lower $C_1$-$C_5$ alcohol is 60-95%.

13. The method of claim 11, wherein the concentration of the aqueous ethanol is 95%.

14. The method of claim 11, wherein the aqueous ethanol has a concentration of 60-95%.

* * * * *

UNITED STATES PATENT AND TRADEMARK OFFICE
CERTIFICATE OF CORRECTION

| | | |
|---|---|---|
| PATENT NO. | : 7,641,922 B2 | Page 1 of 1 |
| APPLICATION NO. | : 10/515963 | |
| DATED | : January 5, 2010 | |
| INVENTOR(S) | : Wei et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1136 days.

Signed and Sealed this

Sixteenth Day of November, 2010

David J. Kappos
*Director of the United States Patent and Trademark Office*